(12) United States Patent
Laghi

(10) Patent No.: US 6,827,744 B1
(45) Date of Patent: Dec. 7, 2004

(54) DYNAMIC PROSTHETIC FOOT WITH MULTIPLE LOAD POINTS AND SINGLE UPPER

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 139 days.

(21) Appl. No.: 10/064,837

(22) Filed: Aug. 22, 2002

(51) Int. Cl.$^7$ .................................................. A61F 2/66
(52) U.S. Cl. ....................................................... 623/53
(58) Field of Search .............................. 623/53, 55, 50, 623/52, 47, 49

(56) References Cited

U.S. PATENT DOCUMENTS

| | | | | |
|---|---|---|---|---|
| 4,994,086 A | * | 2/1991 | Edwards ....................... | 623/26 |
| 5,116,384 A | * | 5/1992 | Wilson et al. ................. | 623/49 |
| 5,156,631 A | * | 10/1992 | Merlette ....................... | 623/52 |
| 5,258,038 A | * | 11/1993 | Robinson et al. ............. | 623/49 |
| 5,258,039 A | * | 11/1993 | Goh et al. ..................... | 623/55 |
| 5,314,499 A | * | 5/1994 | Collier, Jr. .................... | 623/47 |
| 5,376,141 A | * | 12/1994 | Phillips ........................ | 623/55 |
| 5,653,767 A | * | 8/1997 | Allen et al. ................... | 623/52 |
| 5,695,527 A | * | 12/1997 | Allen ............................ | 623/55 |
| 5,776,205 A | * | 7/1998 | Phillips ........................ | 623/55 |
| 5,800,570 A | * | 9/1998 | Collier ......................... | 623/55 |
| 5,944,760 A | * | 8/1999 | Christensen .................. | 623/55 |
| 6,197,068 B1 | * | 3/2001 | Christensen .................. | 623/55 |
| 6,602,295 B1 | * | 8/2003 | Doddroe et al. .............. | 623/55 |
| 6,663,672 B1 | * | 12/2003 | Laghi ........................... | 623/55 |
| 6,676,708 B1 | * | 1/2004 | Laghi ........................... | 623/52 |
| 6,702,859 B1 | * | 3/2004 | Laghi ........................... | 623/52 |

* cited by examiner

Primary Examiner—Alvin Stewart
(74) Attorney, Agent, or Firm—Ronald E. Smith; Smith & Hopen, P.A.

(57) ABSTRACT

A dynamic prosthetic foot having multiple load points includes a sole and an upper member that overlies the sole. A heel end of the upper member has a gradual ninety degree bend formed in so that it is normal to the sole. A longitudinally-extending slot divides the heel end of the upper member into a lateral pylon support and a medial pylon support. The lateral pylon support is thicker than the medial pylon support so that forces applied to the lateral and medial pylons are transferred to a greater extent to the medial pylon support. Vertical bounce during heel strike is eliminated, as is the flat spot. The foot further provides medial lateral stiffness, medial lateral stability, torsional flex and anysotropic stiffness. In a second embodiment, an elongate lateral and medial pylon replace the lateral and medial pylon supports, respectively.

20 Claims, 6 Drawing Sheets

DYNAMIC PROSTHETIC FOOT WITH MULTIPLE LOAD POINTS AND SINGLE UPPER

BACKGROUND OF INVENTION

1. Field of the Invention

This invention relates, generally, to the art of prosthetics. More particularly, it relates to improvements in prosthetic feet.

2. Description of the Prior Art

During normal ambulation, the first part of a foot to contact the ground is the free end of the heel. This initial contact between heel and ground is known as the "heel strike." The free end of the heel is soft and thus cushions the heel strike to at least some extent. The hard bottom of the heel is the next part of the foot to strike the ground; its hardness allows it to support the entire weight of the body. The foot continues to rotate in the well-known way until the toes "push off" at the end of a step.

Early prosthetic feet were quite rigid and provided little or no cushion to the impact on the ground at the moment of "heel strike" and little or no elastic response at "push off." The shock of impact was thus transmitted directly to the skeletal structure of the user, and the lack of elastic response forced an unnatural gait.

Perhaps the earliest prosthetic foot that provided an elastic response at heel strike and push off is disclosed in U.S. Pat. No. 4,547,913 to Phillips, assigned to Flex Foot, Inc. Multiple versions of that device have been developed. The original version is formed of a carbon fiber epoxy matrix consisting of a one-piece combination pylon upper and a one-piece sole. Mechanical fasteners interconnect the upper and the sole. In a second embodiment, the pylon is a round hollow tube and is connected by mechanical fasteners to a rectangular-shaped upper. A third version is like the first except that a standard Sach® foot adapter is employed to connect a standard prosthetic pylon. A fourth version is like the third but has a slightly different geometry. In a fifth version, an elastomeric glue connects the upper and the sole. In additional embodiments, leaf springs or hydraulic cylinders are incorporated into the prosthetic foot.

Although the developments in the art since the mid 1980s have significantly advanced the technology of prosthetic feet, the known prosthetic feet still provide little or no heel elasticity in a direction parallel to the ground. Instead, they provide elastic response in a vertical plane. Thus, although the impact at heel strike is reduced vis a vis the pre-1980's prosthetic feet, the reduced impact is transmitted vertically to the skeletal structure of the user, and the elastic response in a vertical plane-causes a four to six millimeter bounce at heel strike. This vertical response causes an unnatural walk because a healthy human heel is soft at the back or free end where heel strike occurs and is hard on the bottom so that it can support the entire weight of the body. Thus, the normal gait of a human includes a rolling motion as the back of the heel strikes the ground; there is no vertical motion causing the heel to bounce upon ground impact. Accordingly, there remains a need for a prosthetic foot that provides substantial heel elasticity in a direction parallel to the ground.

A healthy human foot rolls on the lateral part of the foot during ambulation. The medial part of the foot provides a cushion and the force required at push off. Thus, there is a smooth transition from heel strike to push off, with no vertical dynamic response of the type that could cause the foot to bounce. Prosthetic feet of the type heretofore known, however, do not provide a smooth transition from heel strike to push off. This lack of a smooth transition produces what is known in the industry as a "flat spot." The presence of a flat spot between heel strike and push off produces an unnatural gait.

More particularly, the dynamic response is primarily vertical at the heel and the toe of a prosthetic foot. There is little or no component of the dynamic response in a horizontal plane as present in a healthy natural foot. The absence of dynamic response in a horizontal plane results in a step like motion going from an elastic vertical motion at heel strike to little or no support at mid-stance (the flat spot), and then again to an elastic vertical motion at push off.

There is a need, therefore, for a prosthetic foot having a dynamic response in a horizontal plane during heel strike, that provides a smooth transition between heel strike and push off to eliminate the flat spot, and that provides a dynamic response in a horizontal plane during push off.

The human foot provides a more rigid support laterally than medially. This design is advantageous because when an instability occurs, the weight of the person shifts from the rigid outer or lateral edge of the foot to the less, rigid inner or medial edge. In this way, the prosthetic foot takes advantage of the presence of the natural foot, i.e., the lateral-to-medial motion experienced at the moment of an instability shifts additional support duties to the natural foot. One major drawback of the heretofore known prosthetic feet is the fact that such feet provide an exactly vertical response during ambulation with no component toward the medial section of the foot. Thus, if an instability in one foot urges the person to fall away from the natural foot, there is no shift of weight toward the medial part of the prosthetic foot as would occur in a natural foot, and the likelihood of a fall is substantially increased.

A prosthetic foot is therefore needed that has differentiated medial and lateral stiffness so that it can respond to instabilities in much the same way as a natural foot.

The single pylon structures of the prior art also exhibit a relatively high torsional stiffness.

Accordingly, there is a need for an improved prosthetic foot that exhibits a lower torsional stiffness when compared to the prosthetic feet of the prior art.

Early prosthetic feet also have a poor rollover motion. Thus there is a need for a prosthetic foot having an improved rollover motion.

Yet another drawback of early prosthetic feet is that they include surfaces that wear against one another, making unwanted noises and wearing out at an accelerated pace.

There is a need, therefore, for a prosthetic foot that has no surfaces that rub against one another, thereby producing a substantially noise-free foot having increased durability.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for a dynamic prosthetic foot is now met by a new, useful, and nonobvious dynamic prosthetic foot having multiple load points and a single upper. The novel foot includes a sole having a heel end and a toe end that are in substantially coplanar relation to one another.

An upper member having a heel end and a toe end overlies the sole. The heel end of the upper member has a gradual ninety degree bend formed therein. The heel end of the upper member separates from the sole along a parting line that is transverse to a longitudinal axis of the prosthetic foot.

A slot is formed in the heel end of the upper member. The slot is substantially coincident with the longitudinal axis of the prosthetic foot and the slot extends from an uppermost end of the heel end of the upper member to a preselected point in the gradual ninety degree bend. The slot divides the heel end into a pair of flat, transversely spaced apart, pylon supports. The pylon supports, including a lateral pylon support and a medial pylon support, are disposed substantially perpendicular to the sole.

A lateral pylon connector adapted to receive a lateral pylon of a prosthetic leg is secured to a trailing end of the lateral pylon support. A medial pylon connector adapted to receive a medial pylon of a prosthetic leg is secured to a trailing end of the medial pylon support. Accordingly, forces acting on the lateral pylon connector are substantially confined to the lateral section of the upper member and forces acting on the medial pylon connector are substantially confined to the medial section of the upper member.

The lateral pylon support has a greater thickness than the medial pylon and the medial section of the upper member. The greater thickness imparts greater stiffness so that forces applied to the lateral pylon support and the medial pylon support are transferred more to the medial pylon support and the medial section of the upper member than to the lateral pylon support and the lateral section of the upper member, thereby mimicking the reaction of a natural foot to forces applied thereto.

Forces acting on the lateral pylon support are therefore transferred at least in part to the medial pylon support and forces acting on the medial pylon support are substantially confined to the medial pylon support.

The sole has a first convexity formed in the heel end that performs the function of the bottom of a natural heel. The sole has a concavity longitudinally spaced from the first convexity, said concavity performing the function of a natural arch. The sole has a second convexity longitudinally spaced from the concavity, said second convexity performing the function of the ball of a natural foot.

The transverse parting line where the heel end of the upper member separates from the sole is positioned substantially in juxtaposition with the bight of the concavity formed in the sole that performs the function of the arch of a natural foot.

In an alternative embodiment, the upper member and sole are integrally formed with one another from said transverse parting line to the toe end of the sole.

In a second embodiment, a pair of elongate pylons that interconnect the prosthetic foot and a prosthetic socket supplants the pylon supports and connectors.

An important object of this invention is to provide a prosthetic foot having heel elasticity in a direction parallel to the ground.

Another important object is to provide a prosthetic foot having a smooth transition from heel strike to push off.

Yet another object is to provide a prosthetic foot having differentiated medial and lateral stiffness so that an instability tends to shift weight from the lateral edge of the prosthetic foot to the medial edge thereof, just as in a natural foot.

Still further objects are to provide a prosthetic foot having medial/lateral stability, torsional flex, and anysotropic stiffness.

Another important object is to provide a prosthetic foot having an improved rollover motion.

Another major object is to provide a prosthetic foot that exhibits lower torsional stiffness than a prosthetic foot having a conventional pylon.

Another object is to achieve the preceding object by providing a prosthetic foot having multiple pylon supports or pylons.

Still another object is to provide a prosthetic foot having no parts that wear against one another, thereby providing a substantially noise-free prosthetic foot having increased durability vis a vis conventional prosthetic feet.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
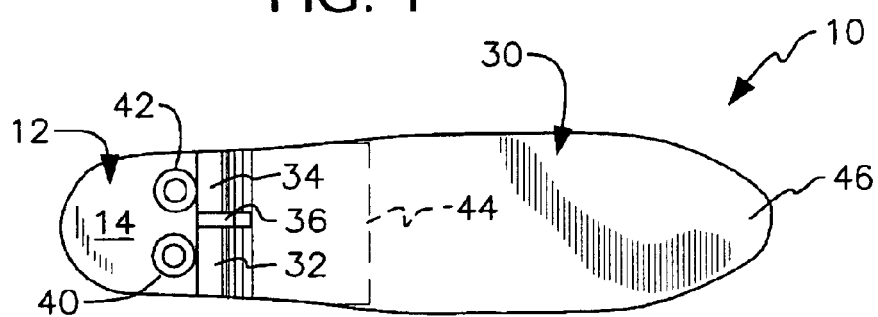
FIG. 1 is a top plan view of a prosthetic foot with multiple load points and a single upper and having truncate pylon supports.
Figure 2:
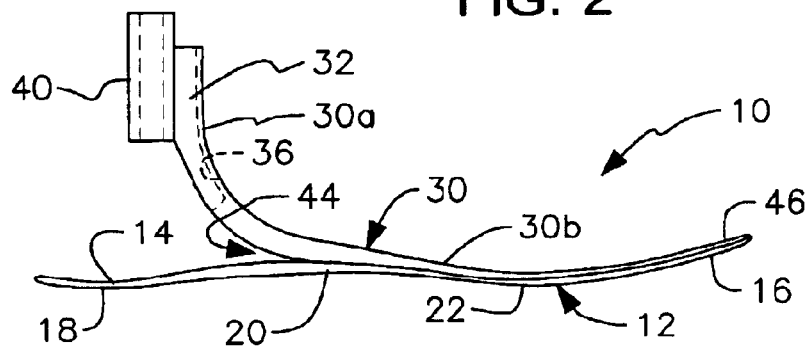
FIG. 2 is a side elevational view thereof.
Figure 3:
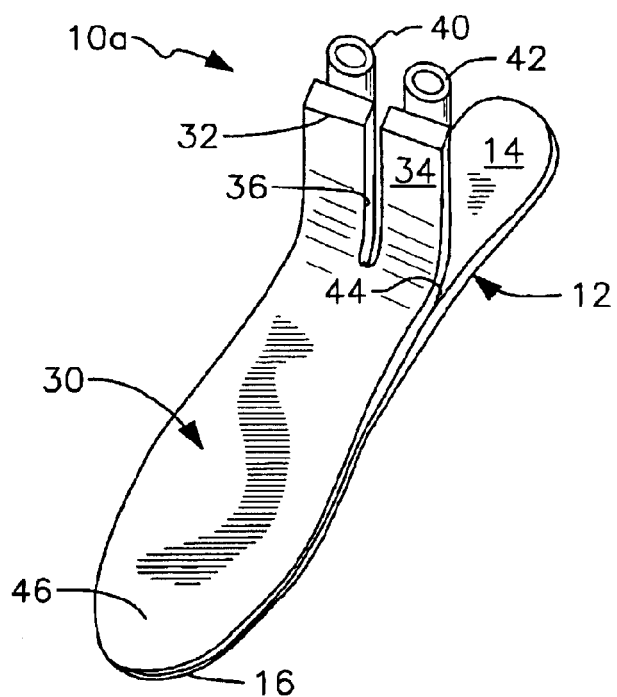
FIG. 3 is a perspective view thereof.

Referring to FIGS. 1–3, it will there be seen that the reference numeral 10 denotes an illustrative embodiment of the novel dynamic prosthetic foot having multiple load points and a single upper.

Prosthetic foot 10 includes a sole 12 having a heel end 14 and a toe end 16 that are in substantially coplanar relation to one another. Relative to the ground, as best understood in connection with FIG. 2, sole 12 includes first convexity 18 that performs the function of the bottom of a natural heel, concavity 20 that performs the function of a natural arch, and second convexity 22 that performs the function of the ball of a natural foot.

Upper member 30 includes a pair of flat, transversely spaced apart, pylon supports 32, 34 that are separated from one another by longitudinally extending slot 36. Lateral pylon support 32 has a greater thickness than medial pylon support 34 as indicated in FIGS. 1 and 3.

Pylon connectors 40, 42 are attached to pylons 32, 34, respectively, preferably on a trailing (heel) side thereof, and an elongate pylon, not shown in FIGS. 1–3, is then engaged to each pylon connector.

Transverse parting line 44 indicates where upper member 30 separates from sole 12. As indicated by a comparison of FIGS. 1 and 2, said parting line in is juxtaposition with the bight of in concavity 20. Significantly, transverse parting line 44 also divides a toe end of upper member 30 from a heel end of upper member 30. A gradual ninety degree (90°) bend begins at said transverse parting line. Accordingly, the toe end of upper member 30 is disposed at a substantially ninety degree (90°) angle to the heel end of the upper member. As best depicted in FIG. 2, longitudinally-extending slot 36 extends from the uppermost end of the top member heel end to a point about mid-way of the gradual ninety degree (90°) bend. Slot 36 thus stops well short of the toe end of top member 30.

Slot 36 has a first end in open communication with the respective free ends of pylon supports 32, 34, as perhaps best depicted in FIG. 3. The second end of slot 36 terminates about half way through the curvature that connects sole 30 and said pylon supports 32, 34. In other words, slot 36 terminates about mid-length of the bight that connects sole 30 and said pylon supports 32, 34, as perhaps best understood in connection with FIG. 2.

The greater thickness and thus greater stiffness of lateral pylon support 32 ensures that instabilities appearing on foot 10 will be shifted in a medial direction, just like a natural foot. Slot 36 enables lateral pylon support 32 to respond to instabilities substantially independently of medial pylon support 34, and vice versa. In other words, any force transferred from the lateral pylon support is substantially attenuated when transmitted to the medial pylon support, and vice versa.

Pylon supports 32, 34 are curved as depicted so that their respective lower ends gradually join upper member 30 at a transverse parting line 44 that is about mid-length of arch concavity 20. Upper members 30a and 30b overlie and abut sole 12 from parting line 44 to toe end 46 thereof. The thickness of upper members 30a and 30b gradually decrease as depicted as they extend from transverse parting line 44 to said toe end. The combined thickness of sole 12 and upper member 30 at said toe end is substantially the same as the thickness of the heel end 14 of sole 12. The elastic response of said heel and toe ends of said sole 12 are thus controlled by the thickness of the sole and the upper member to provide differentiating elastic response for patients of differing weights, differing activity levels, or both.

Figure 4:
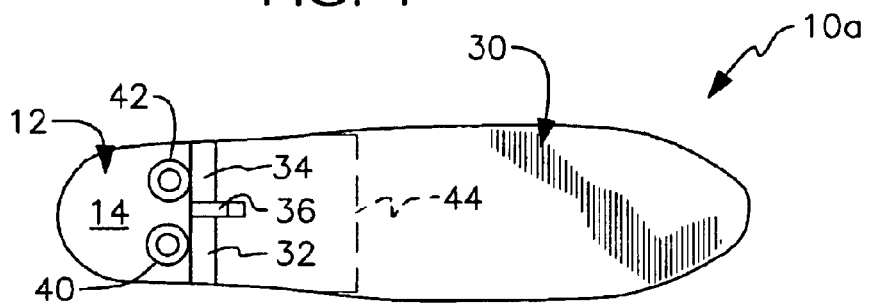
FIG. 4 is a top plan view of a second embodiment of the prosthetic foot of FIG. 1.
Figure 5:
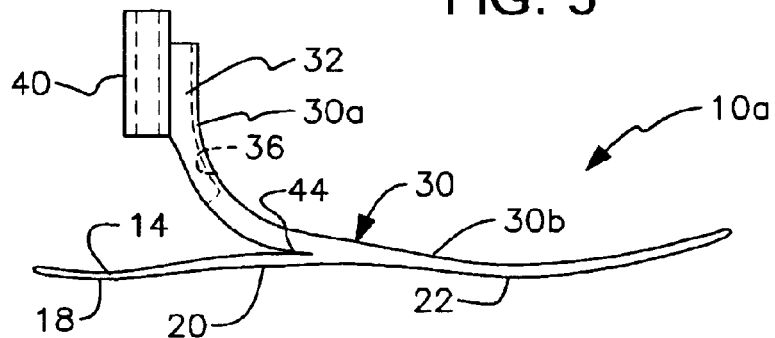
FIG. 5 is a side elevational view of said FIG. 4 second embodiment.
Figure 6:
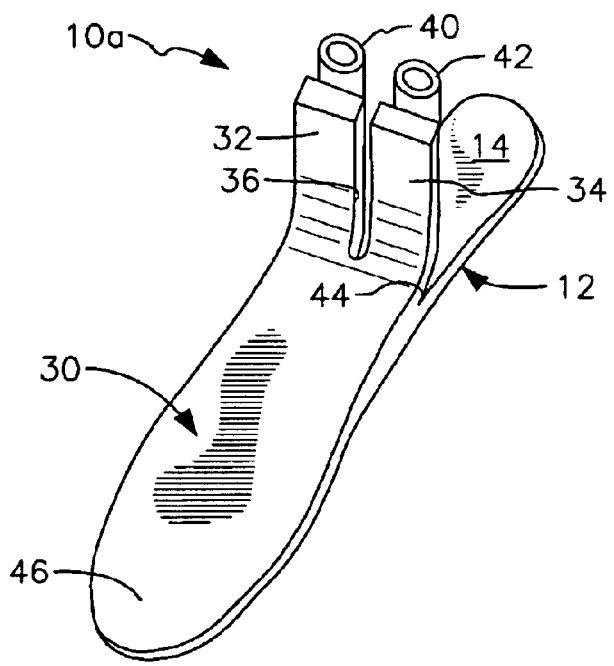
FIG. 6 is a perspective view of said FIG. 4 second embodiment.

The alternative embodiment of FIGS. 4–6 is like the embodiment of FIGS. 1–3 in all respects except that sole 12 and the part of upper member 30 between transverse parting line 44 and toe 46 are of unitary construction in said alternative embodiment, i.e., said parts are integrally formed with one another as depicted.

Figure 7:
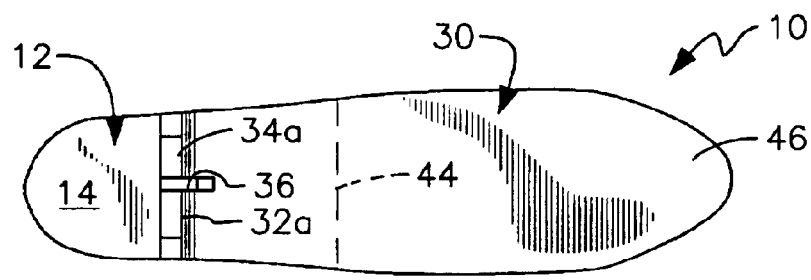
FIG. 7 is a top plan view of a prosthetic foot with multiple load points and a single upper and having elongate pylons.
Figure 8:
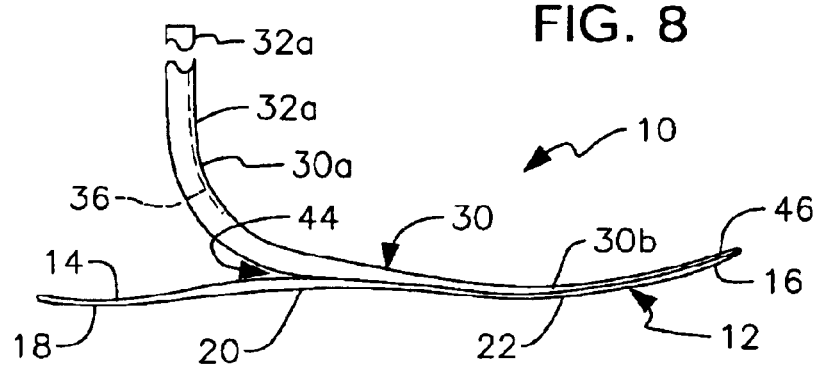
FIG. 8 is a side elevational view thereof.
Figure 9:
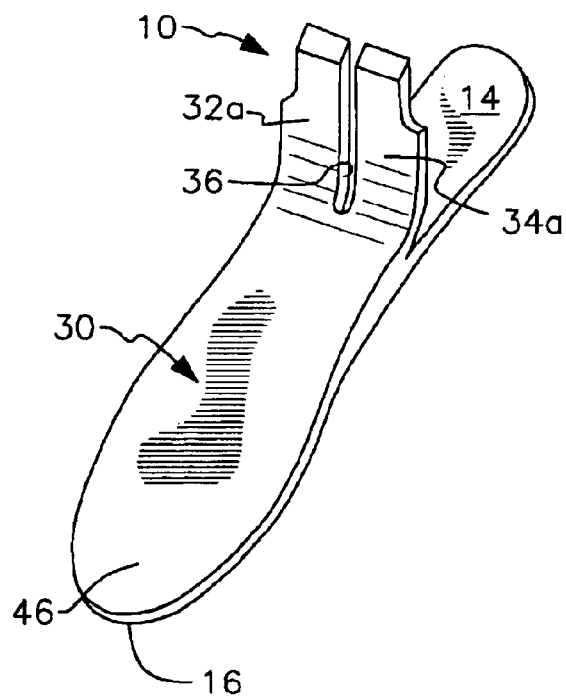
FIG. 9 is a perspective view thereof.

The embodiment of FIGS. 7–9 differs from the embodiment of FIGS. 1–3 in that pylon supports 32, 34 are now elongate pylons 32a, 34a having a length of about twenty inches (20'). This eliminates the need for pylon connectors 40, 42. A prosthetist cuts pylons 32a, 34a to size when the patient is fitted with the novel prosthetic foot.

Figure 10:
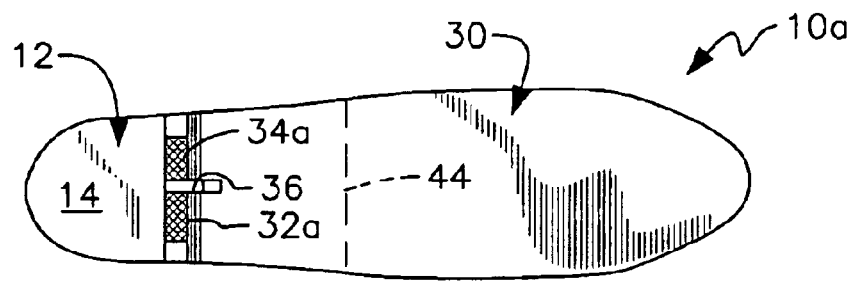
FIG. 10 is a top plan view of a second embodiment of the prosthetic foot of FIG. 7.
Figure 11:
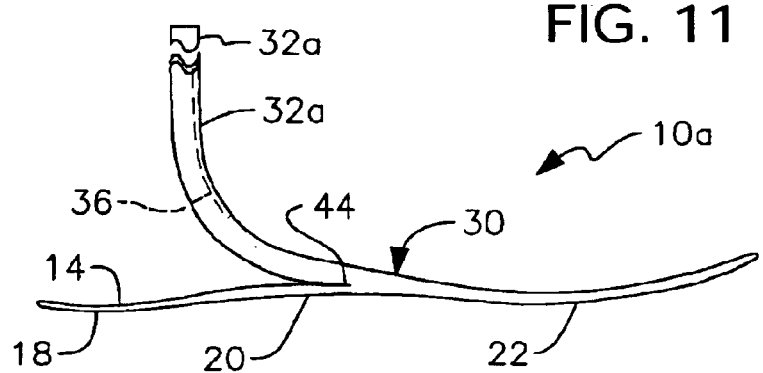
FIG. 11 is a side elevational view of said FIG. 10 second embodiment.
Figure 12:
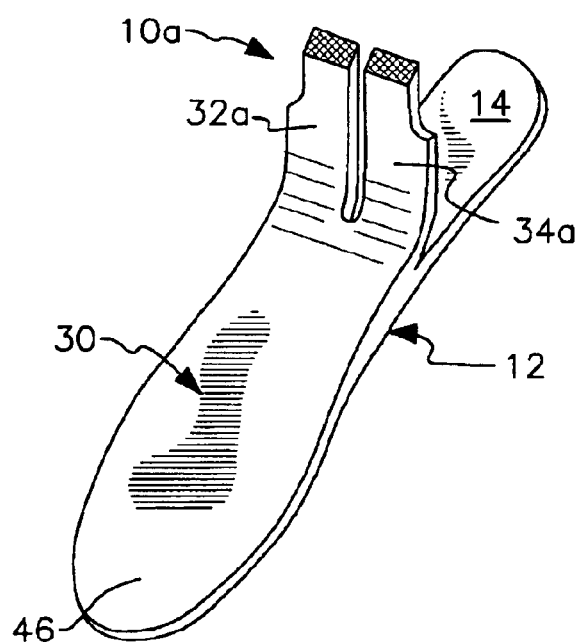
FIG. 12 is a perspective view of said FIG. 10 second embodiment.

The embodiment of FIGS. 10–12 similarly differs from the embodiment of FIGS. 4–6 in that pylon supports 32, 34 are now elongate pylons 32a, 34a having a length of about twenty inches (20"). This eliminates the need for pylon connectors 40, 42.

Figure 13:
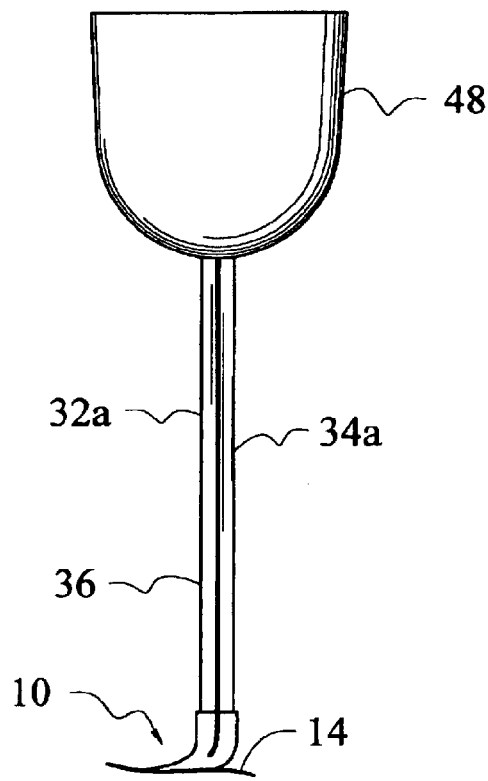
FIG. 13 is a perspective view of the elongate pylons embodiment when attached to a socket.

FIG. 13 depicts the novel structure when equipped with elongate pylons 32a, 34a.

After pylons 32a, 34a have been cut to a desired length, the prosthetist has several options by which the pylons may be connected to prosthetic socket 48. Pylons 32a, 34a may be laminated into prosthetic socket 48 as illustrated in said FIG. 13. This forms a permanent connection between pylons 32a, 34a and socket 48.

Figure 14:
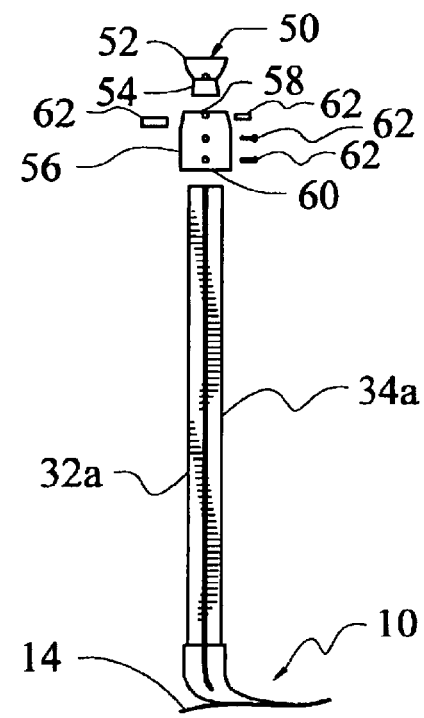
FIG. 14 is a perspective view of the elongate pylons embodiment and further depicting connector means, in exploded form, for connecting said elongate pylons to a socket.

A second option includes the use of a commercially available pyramid connector 50 as depicted in FIG. 14. Such pyramid connectors have been in use for fifty or so years. Pyramid connector 50 includes upper part 52 and lower part 54 that depends from the upper part. Upper part 52 is attached to the lowermost or distal end of socket 48. A hollow pyramid-receiving connector 56 has an open upper end 58 that receives lower part 54 of pyramid connector 50 and an open lower end 60 that receives the respective uppermost ends of pylons 32a, 34a. Lower end 54 of pyramid connector 50 and the respective upper ends of pylons 32a, 34a are captured in said hollow pyramid-receiving connector 56 by a plurality of set screws and other suitable fastening means, collectively denoted 62.

Pyramid connector 52 and pyramid-receiving connector 56 are employed to enable adjustment of the angle of pylons 32a, 34a so that prosthetic foot 10 falls in the correct medial/lateral and anterior/posterior planes, as perhaps best understood by making reference to FIG. 14.

A third option available to the prosthetist after cutting pylons 32a, 34a to their correct length is to laminate the pylons to an unillustrated component and to attach that component to the socket.

Figure 15A:
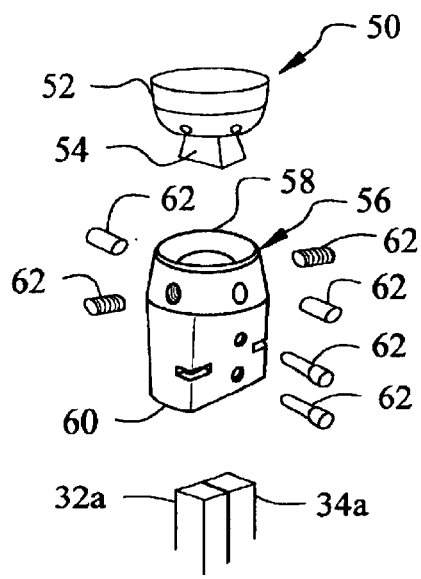
FIG. 15A is an exploded first perspective view of said connector means.
Figure 15B:
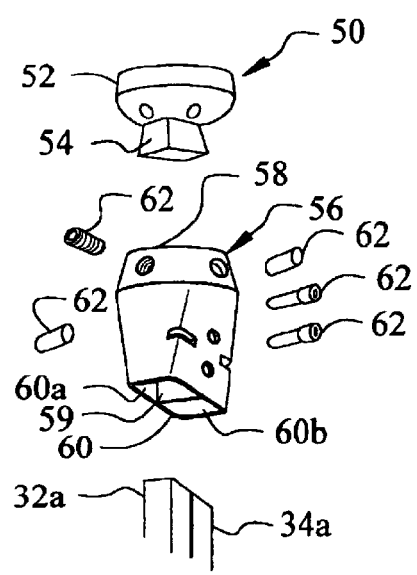
FIG. 15B is an exploded second perspective view of said connector means.
Figure 15C:
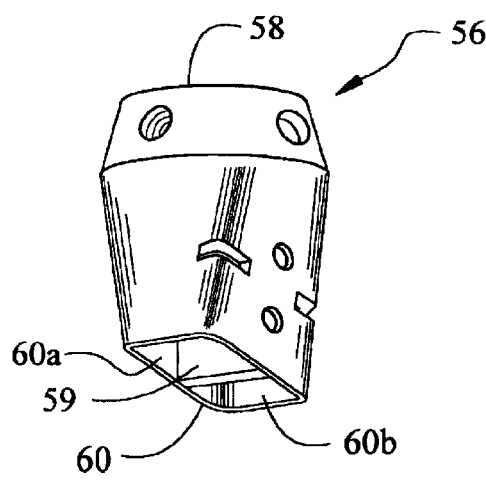
FIG. 15C is a first perspective view of a pyramid-receiving connector.
Figure 15D:
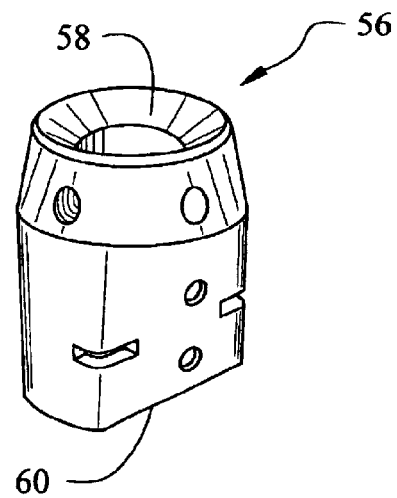
FIG. 15D is a second perspective view of said pyramid-receiving connector.

FIGS. 15A and 15B provide a more detailed perspective view of pyramid connector 50 and pyramid-receiving connector 56. FIGS. 15C and 15D provide a more detailed view of pyramid receiving connector 56. Partition wall 59 divides open lower end 60 of pyramid-receiving connector 56 into compartments 60a, 60b for receiving pylons 32a, 34a, respectively.

In all embodiments, the thickness of upper member 30a is substantially different than the thickness of upper member 30b to provide a controlled elastic response. More specifically, it shifts loads to the medial section providing the function of eliminating the flat spot of earlier prosthetic feet because such construction provides a smooth transition from heel strike to push off. Moreover, the bifurcated construction of pylon supports 32, 34 (FIGS. 1–6) or pylons 32a, 34a (FIGS. 7–12) and the greater thickness of lateral pylon support 32 (FIGS. 1–6) or pylon 32a (FIGS. 7–12) and lateral upper member 30a enhance the stability of the user because said greater thickness serves to shift the weight of the user toward the medial side of the foot and thus harnesses the stabilizing power of the sound foot that opposes the prosthetic foot.

The novel structure further enhances the lateral stability, the torsional flex, and the anisotropic stiffness of foot 10.

The reduced torsional stiffness provided by the double pylons of this invention is of major significance. Some torsion in the shin is desirable. More precisely, torsion that can be controlled by the thickness and geometry of the cross section is advantageous over completely rigid pylons. The double pylons of this invention, each of which has a cross section of preselected size, enable the prosthesis user to participate in sporting activities such as golf.

Moreover, the novel foot can flex in the medial plane without having relative moving parts. This represents one of the major breakthroughs of this invention.

Advantageously, heel 14 provides a dynamic response in the horizontal plane during heel strike. This heel elasticity eliminates the vertical bounce caused by the dynamic response in the vertical plane of prior art prosthetic feet. The merging of pylon supports 32, 34 (FIGS. 1–6) or pylons 32a, 34a (FIGS. 7–12) with sole 12 at transverse parting line 44 about mid-length of arch 20 eliminates the flat spot of earlier prosthetic feet because such construction provides a smooth transition from heel strike to push off. Moreover, the bifurcated construction of pylon supports 32, 34 (FIGS. 1–6) or pylons 32a, 34a (FIGS. 7–12) and the greater thickness of lateral pylon support 32 or lateral pylon 32a and lateral side 30a of the upper member enhances the stability of the user because said greater thickness serves to shift the weight of the user toward the medial side of the foot and thus harnesses the stabilizing power of the sound foot that opposes the prosthetic foot.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall there between.

What is claimed is:

1. A dynamic prosthetic foot having multiple load points and a single upper, comprising:
    a sole having a heel end and a toe end that are in substantial coplanar relation to one another;
    an upper member that overlies said sole, said upper member having a heel end and a toe end;
    said upper member having a gradual ninety degree bend formed therein, said gradual ninety degree bend separating said toe end of said upper member from said heel end of said upper member, said heel end of said upper member separating from said toe end of said upper member along a parting line that is transverse to a longitudinal axis of said prosthetic foot;
    a slot formed in said heel end of said upper member, said slot substantially coincident with the longitudinal axis of said prosthetic foot and said slot extending from an uppermost end of said heel end of said upper member to a point about mid-way of said gradual ninety degree bend;
    said slot dividing said heel end of said top member into a lateral pylon support and a lateral section of said upper member and into a medial pylon support and a medial section of said upper member;
    said pylon supports being disposed substantially perpendicular to said sole;
    whereby forces acting on said lateral pylon support are substantially confined to said lateral pylon support and said lateral section of said upper member and forces acting on said medial pylon support are substantially confined to said medial pylon support and said medial section of said upper member;
    whereby forces acting upon said lateral section of said upper member are substantially attenuated when transmitted to the medial section of said upper section; and
    whereby forces acting upon said medial section of said upper member are substantially attenuated when transmitted to the lateral section of said upper section.

2. The dynamic prosthetic foot of claim 1, further comprising:
    said lateral pylon support having a greater thickness than said medial pylon support;
    said greater thickness imparting greater stiffness so that forces applied to said lateral pylon support and said medial pylon support are applied more to said medial pylon support than to said lateral pylon support, thereby mimicking the reaction of a natural foot to forces applied thereto.

3. The dynamic prosthetic foot of claim 1, wherein said lateral section of said lateral upper member has a greater thickness than said medial section of said medial upper member, said greater thickness imparting greater strength so that forces applied to said lateral upper member are provided with less of an elastic response than forces applied to said medial upper member, thereby mimicking the reaction of a natural foot to forces applied thereto.

4. The dynamic prosthetic foot of claim 1, wherein said sole has a first convexity formed in said heel end that performs the function of the bottom of a natural heel.

5. The dynamic prosthetic foot of claim 4, wherein said sole has a concavity longitudinally spaced from said first convexity, said concavity performing the function of a natural arch, and wherein said parting line is in juxtaposition with a bight of said concavity.

6. The dynamic prosthetic foot of claim 5, wherein said sole has a second convexity longitudinally spaced from said concavity, said second convexity performing the function of the ball of a natural foot.

7. The dynamic prosthetic foot of claim 6, wherein said point is an inflection point where a downward slope of said concavity meets an upward slope of said second convexity.

8. The dynamic prosthetic foot of claim 1, further comprising a pylon connector secured to each of said pylon supports on a trailing side thereof.

9. The dynamic prosthetic foot of claim 1, wherein said sole and a said toe end of said upper member are formed integrally with one another.

10. A dynamic prosthetic foot having multiple load points and a single upper, comprising:
    a sole having a heel end and a toe end in substantially coplanar relation with one another;
    an upper member that overlies said sole, said upper member having a heel end and a toe end;
    said upper member having a gradual ninety degree bend formed therein, said gradual ninety degree bend separating a toe end of said upper member from a heel end of said upper member, said heel end of said upper member separating from said see toe end of said upper member along a parting line that is transverse to a longitudinal axis of said prosthetic foot;

a slot formed in said heel end of said upper member, said slot substantially coincident with a longitudinal axis of said prosthetic foot and said slot extending from an uppermost end of said heel end of said upper member to a point about mid-way of said gradual ninety degree bend;

said slot dividing said heel end of said top member into a lateral pylon and a lateral section of said upper member and into a medial pylon and a medial section of said upper member;

said lateral and medial pylons being disposed substantially perpendicular to said sole;

said lateral and medial pylons having a common length sufficient to interconnect said prosthetic foot and a prosthetic socket;

whereby forces acting on said lateral pylon support are substantially confined to said lateral pylon support and said lateral section of said upper member and forces acting on said medial pylon support are substantially confined to said medial pylon support and said medial section of said upper member;

whereby forces acting upon said lateral section of said upper member are substantially attenuated when transmitted to the medial section of said upper section; and whereby forces acting upon said medial section of said upper member are substantially attenuated when transmitted to the lateral section of said upper section.

11. The dynamic prosthetic foot of claim 10, further comprising:

said lateral pylon having a greater thickness than said medial pylon;

said greater thickness imparting greater stiffness so that forces applied to said lateral pylon and said medial pylon are applied more to said medial pylon than to said lateral pylon, thereby mimicking the reaction of a natural foot to forces applied thereto.

12. The dynamic prosthetic foot of claim 10, wherein said lateral section of said lateral upper member has a greater thickness than said medial section of said medial upper member, said greater thickness imparting greater strength so that forces applied to said lateral upper member are met with less of an elastic response than forces applied to said medial upper member, thereby mimicking the reaction of a natural foot to forces applied thereto.

13. The dynamic prosthetic foot of claim 10, wherein said sole has a first convexity formed in said heel end that performs the function of the bottom of a natural heel.

14. The dynamic prosthetic foot of claim 13, wherein said sole has a concavity longitudinally spaced from said first convexity, said concavity performing the function of a natural arch, and said parting line being in juxtaposition with a bight of said concavity.

15. The dynamic prosthetic foot of claim 14, wherein said sole has a second convexity longitudinally spaced from said concavity, said second convexity performing the function of the ball of a natural foot.

16. The dynamic prosthetic foot of claim 15, wherein said point is an inflection point where a downward slope of said concavity meets an upward slope of said second convexity.

17. The dynamic prosthetic foot of claim 10, wherein said sole and and said toe end of said upper member are formed integrally with one another.

18. The dynamic prosthetic foot of claim 10, wherein said lateral and medial pylons are laminated at respective uppermost ends thereof to a prosthetic socket.

19. The dynamic prosthetic foot of claim 10, wherein said lateral and medial pylons are connected at respective uppermost ends thereof to a connector member and wherein said connector member is laminated to a prosthetic socket.

20. The dynamic prosthetic foot of claim 10, wherein said lateral and medial pylons are connected at respective uppermost ends thereof to a pyramid-receiving connector that engages a pyramid that depends from said prosthetic socket.

* * * * *